United States Patent [19]

Wright et al.

[11] 4,260,890

[45] Apr. 7, 1981

[54] FLUORESCENT GAS ANALYZER

[75] Inventors: Steven A. Wright, San Diego; Donald A. Watts, Ramona, both of Calif.

[73] Assignee: Monitor Labs, Incorporated, San Diego, Calif.

[21] Appl. No.: 51,498

[22] Filed: Jun. 25, 1979

[51] Int. Cl.$^3$ .......................... G01J 1/42; G01N 21/64
[52] U.S. Cl. ..................................... 250/373; 250/435
[58] Field of Search .................. 250/372, 373, 432 R, 250/435

[56] References Cited

U.S. PATENT DOCUMENTS

| | | | |
|---|---|---|---|
| 3,826,920 | 7/1974 | Woodroffe et al. | 250/373 |
| 3,845,309 | 10/1974 | Helm et al. | 250/373 |
| 3,906,226 | 9/1975 | Okabe et al. | 250/373 |

OTHER PUBLICATIONS

Schwarz et al., "Fluorescence Detection of Sulfur Dioxide in Air at the Parts per Billion Level", Analytical Chemistry, vol. 46, pp. 1024-1028, Jul. 1974.

Okabe et al., "Ambient Sulfur Dioxide Detector Based on a Fluorescent Method", Presented at 65th Meeting of Air Pollution Control Association at Miami Beach, Florida, Jun. 18-22, 1972.

*Primary Examiner*—Alfred E. Smith
*Assistant Examiner*—Janice A. Howell
*Attorney, Agent, or Firm*—Brown & Martin

[57] ABSTRACT

A fluorescent gas analyzer that provides a DC output signal that is proportional to the concentration of a given gas that fluoresces within a reaction cell over a predetermined interval is disclosed. The analyzer includes a detector combination and a compensation circuit that prevent the output signal from being affected by scattered excitation energy detected by the fluorescence detector or by variations in the excitation energy. The analyzer is particularly adapted for detecting fluorescence from SO$_2$ that is excited by UV radiation.

8 Claims, 4 Drawing Figures

4,260,890

FLUORESCENT GAS ANALYZER

BACKGROUND OF THE INVENTION

The present invention pertains to improvements in fluorescent gas analyzers.

Fluorescent gas analyzers essentially include a reaction cell having inlet and outlet ports for enabling a carrier gas to flow through the cell; an excitation energy source coupled to the reaction cell for radiating the interior of the cell with excitation energy that causes a given gas to fluoresce in a given wavelength; and a detector coupled to the reaction cell for detecting fluorescence in the given wavelength and for providing a signal that is proportional to the intensity of the detected fluorescence. This signal is integrated over a predetermined interval to provide an output signal that is approximately proportional to the concentration of the given gas within the carrier gas cell. 11 Florescent gas analyzers are useful in measuring the concentration of pollutant gases, such as sulfur dioxide ($SO_2$) and nitrogen dioxide ($NO_2$) within various carrier exhaust gases.

Fluorescent detection of $SO_2$ excited by ultraviolet (UV) radiation is discussed in a paper by OKabe et al, entitled "Ambient Sulfur Dioxide Detector Based on a Fluorescent Method", presented at the 65th Meeting of the Air Pollution Control Association at Miami Beach, Fla., June 18-22, 1972, and in Schwarz and OKabe, "Fluorescence Detection of of Sulfur Dioxide in Air at the Parts per Billion Level", Analytical Chemistry, Vol. 46, pp 1024-1028, July 1974. Examples of fluorescent gas analyzers are described in U.S. Pat. Nos. 3,826,920 to Woodroffe et al and 3,845,309 to Helm et al.

The accuracy of prior art fluorescent gas analyzers is impaired by two significant factors. The intensity of the fluorescence and the resultant output signal are dependent upon the intensity of the excitation energy, whereby variations in the excitation energy affect the output signal level. In addition, the fluorescence detector also detects scattered excitation energy, whereby the resultant output signal is proportional to the intensity of the detected fluorescence and the intensity of the detected scattered excitation energy radiated from the excitation energy source.

SUMMARY OF THE INVENTION

The gas analyzer of the present invention includes a combination of detectors and a compensation circuit that prevent the output signal from being affected by scattered excitation energy detected by the fluorescence detector or by variations in the excitation energy.

The fluorescent gas analyzer of the present invention includes a reaction cell having inlet and outlet ports for enabling gas flow through the cell; an excitation energy source coupled to the reaction cell for radiating the interior of the cell with excitation energy that causes a given gas to fluoresce in a given wavelength; and a first detector coupled to the reaction cell for detecting fluorescence in the given wavelength and for providing a first signal that is proportional to the intensity of the detected fluorescence and the intensity of detected scattered excitation energy radiated from the excitation energy source. The fluorescent gas analyzer of the present invention is characterized by the combination of a second detector coupled to the reaction cell for detecting excitation energy radiated from the excitation energy source, and for providing a second signal that is proportional to the detected excitation energy; and a compensation circuit including a first circuit coupled to the first detector for responding to the first signal to provide a third signal having a level bearing a given proportional relationship to the sum of the quantity of the fluorescence detected by the first detector over a predetermined interval and the quantity of the scattered excitation energy detected by the first detector over the predetermined interval; a second circuit coupled to the second detector for responding to the second signal to provide a fourth signal having a level bearing the given proportional relationship to the quantity of the excitation energy detected by the second detector over the predetermined interval; a third circuit coupled to the second circuit for factoring the fourth signal to provide a fifth signal having a level bearing the given proportional relationship to the quantity of the scattered excitation energy detected by the first detector over the predetermined interval; a fourth circuit coupled to the first and third circuits for providing a sixth signal having a level bearing the given proportional relationship to the difference between the levels of the third and fifth signals, to thereby provide a signal having a level bearing the given proportional relationship to the quantity of the fluorescence detected by the first detector over the predetermined interval; and a fifth circuit for dividing the sixth signal by the fourth signal to provide a seventh signal having a level that is proportional to the concentration of the gas that fluoresces within the reaction cell in response to the excitation energy over the predetermined interval.

In the preferred embodiment the third circuit includes a potentiometer for reducing the level of the fourth signal to provide a fifth signal that has a level that causes the level of the seventh signal to be zero when a gas containing no fluorescent compounds is radiated by excitation energy within the reaction cell.

The fluorescent gas analyzer of the present invention is particularly useful for detecting $SO_2$, which is excited into fluorescence by UV radiation; and it also is useful for detecting other fluorescent compounds, such as $NO_2$ and some hydrocarbons.

Additional features of the present invention are described in the Description of the Preferred Embodiment.

DESCRIPTION OF THE PREFERRED EMBODIMENT

Figure 1:
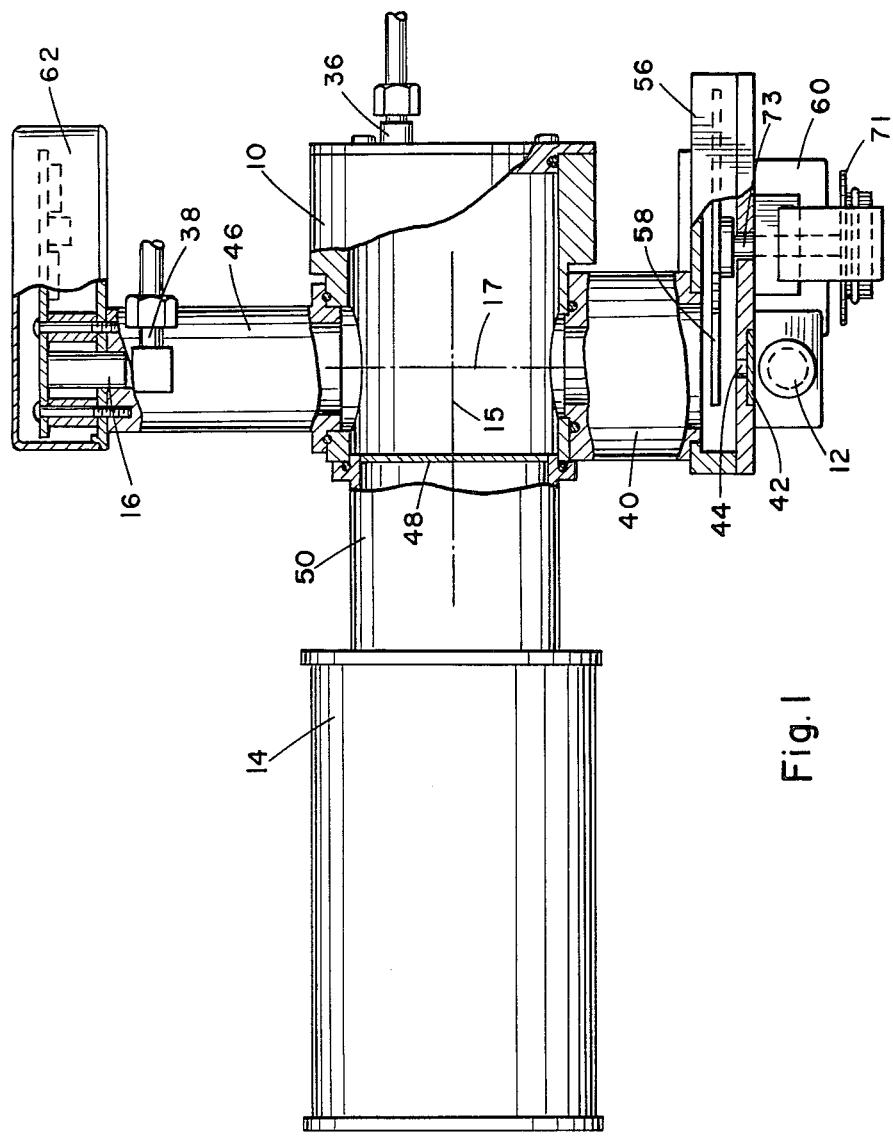
FIG. 1 is a side elevation view of a preferred embodiment of the reaction cell and detector assembly of the fluorescent gas analyzer, with portions cut away.

Referring to the Drawing, the preferred embodiment of the gas analyzer of the present invention essentially includes a reaction cell 10, a UV source, such as a UV lamp 12, a fluorescence detector, such as a photomultiplier tube 14, a photo detector, such as a vacuum photo diode 16, a first signal conditioning circuit 18, a second signal conditioning circuit 20, a first integrator circuit 22, a second integrator circuit 24, a first DC amplifier 26, a second DC amplifier 28, a potentiometer 30, a summing circuit 32, and a divider circuit 34.

The reaction cell 10 has an inlet port 36 and an outlet port 38 for enabling carrier gas to flow through the cell 10.

The UV lamp 12 is coupled to the reaction cell 10 for radiating the interior of the cell 10 with UV light. The UV lamp 12 is coupled to the reaction cell 10 by means of an optical lens cell 40. The UV light radiates from the UV lamp 12 through a UV bandpass filter 42, an aperture 44, the optical lens cell 40 and the reaction cell 10 into a light dump 46, and is collected by the vacuum photo diode 16, which is positioned at the end of the light dump 46. The vacuum photo diode 16 detects only the UV light and is insensitive to the wavelengths of light that fluoresce from compounds within the carrier gas upon excitation by the UV light in the reaction cell 10.

The vacuum photo diode 16 and the UV lamp 12 are coaxially positioned on opposite sides of the reaction cell 10, and the photomultiplier tube 14 is positioned to detect primarily fluorescence along an axis 15 that is orthogonal to the common axis 17 of the diode 16 and the lamp 12.

The photomultiplier tube 14 is coupled to the reaction cell 10 for detecting fluorescence from sulfur dioxide that fluoresces within the reaction cell 10 in response to excitation by UV radiation from the lamp 12. The photomultiplier tube 14 is coupled to the reaction cell by an optical bandpass filler 48 and an optical lens cell 50. The bandpass filter 48 passes primarily only light having the wavelength of fluorescing $SO_2$. However, some scattered UV light still is detected by the photomultiplier tube 14. The photomultiplier tube 14 provides a first signal on line 52 that is proportional to the intensity of the detected fluorescence from the $SO_2$ in the reaction cell 10 and the intensity of detected scattered UV light radiated from the UV lamp 12.

The vacuum photo diode 16 provides a second signal on line 54 that is proportional to the UV light detected by the vacuum photo diode 16.

Figure 3:
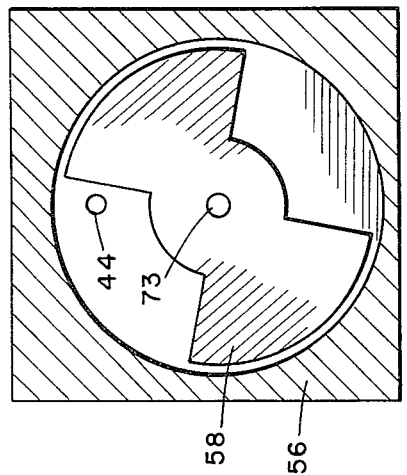
FIG. 3 is a sectional view taken on line 3—3 of FIG. 2.
Figure 2:
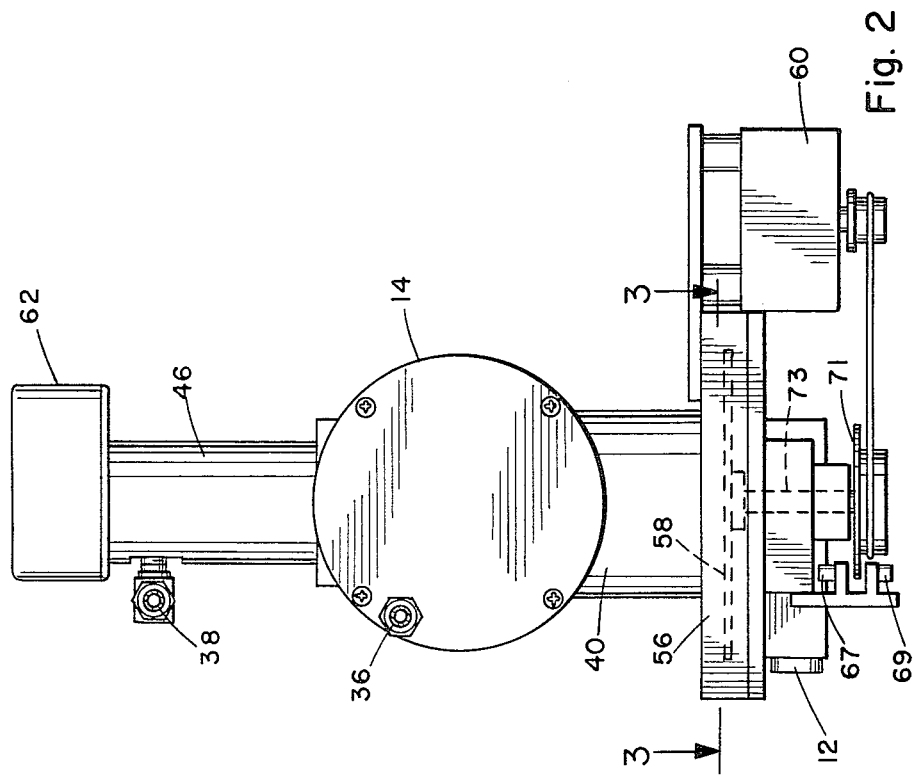
FIG. 2 is an end elevation view of the assembly as taken from the right hand side of FIG. 1.

A chopper 56 is coupled to the UV lamp 12 for causing the UV light that is radiated into the reaction cell 10 to be pulsed at a predetermined rate for enhancing the signal-to-noise ratio of the first and second signals on lines 52 and 54. The chopper 56 is positioned between the aperture 44 and the optical lens cell 40. Although pulsed light could be produced electronically in an alternative embodiment, it is preferred to use a mechanical chopper 56, which includes a chopper disk 58 that is driven by a motor 60. The chopper disk is divided into 90 degree segments, as shown in FIG. 3.

The signal conditioning circuits 18, 20 include preamplifiers, mixers, amplifiers and limiters of standard design. Coarse calibration and range adjustments are connected to the amplifiers. The second signal conditioning circuit 20 is contained in the same housing 62 as the vacuum photo diode 16, which is attached to the light dump 46.

The first and second signal conditioning circuits 18, 20 respectively pass the conditioned first and second signals on lines 64 and 66 to the first integrator 22 and the second integrator 24. The first and second integrators 22, 24 continuously integrate the first and second signals on line 64 and 66 over a predetermined interval.

A synchronizer 68 is coupled to the chopper and the integrators 22, 24 for providing a synchronization signal on line 70 having the predetermined pulse rate of the chopper 56 to the integrators 22, 24 for synchronizing the integration with the pulses of UV light radiated into the reaction cell 10. The synchronizer 68 includes an LED 67, a photodetector 69 and a synchronizer disk 71. The synchronizer disk 71 is mounted on the same shaft 73 as the chopper disk 58 and interrupts the light path between the LED 67 and the photo detector 69 at the same pulse rate as the light from the UV lamp is interrupted by the chopper disk 58.

The first integrator 22 responds to the first signal on line 64 to provide a third signal on line 72 having a level bearing a given proportional relationship to the sum of the quantity of the fluorescence detected by the photomultiplier tube 14 over the predetermined interval and the quantity of the scattered excitation energy detected by the photo multiplier tube 14 over the predetermined interval.

The second integrator 24 responds to the second signal on line 66 to provide a fourth signal on line 74 having a level bearing the given proportional relationship to the quantity of the UV light detected by the vacuum photo diode 16 over the predetermined interval.

The third and fourth signals on lines 72 and 74 are DC signals which are amplified by DC amplifiers 26 and 28 respectively to provide amplified third and fourth signals on lines 76 and 78. A fine calibration adjustment is connected to the DC amplifier 26.

Figure 4:
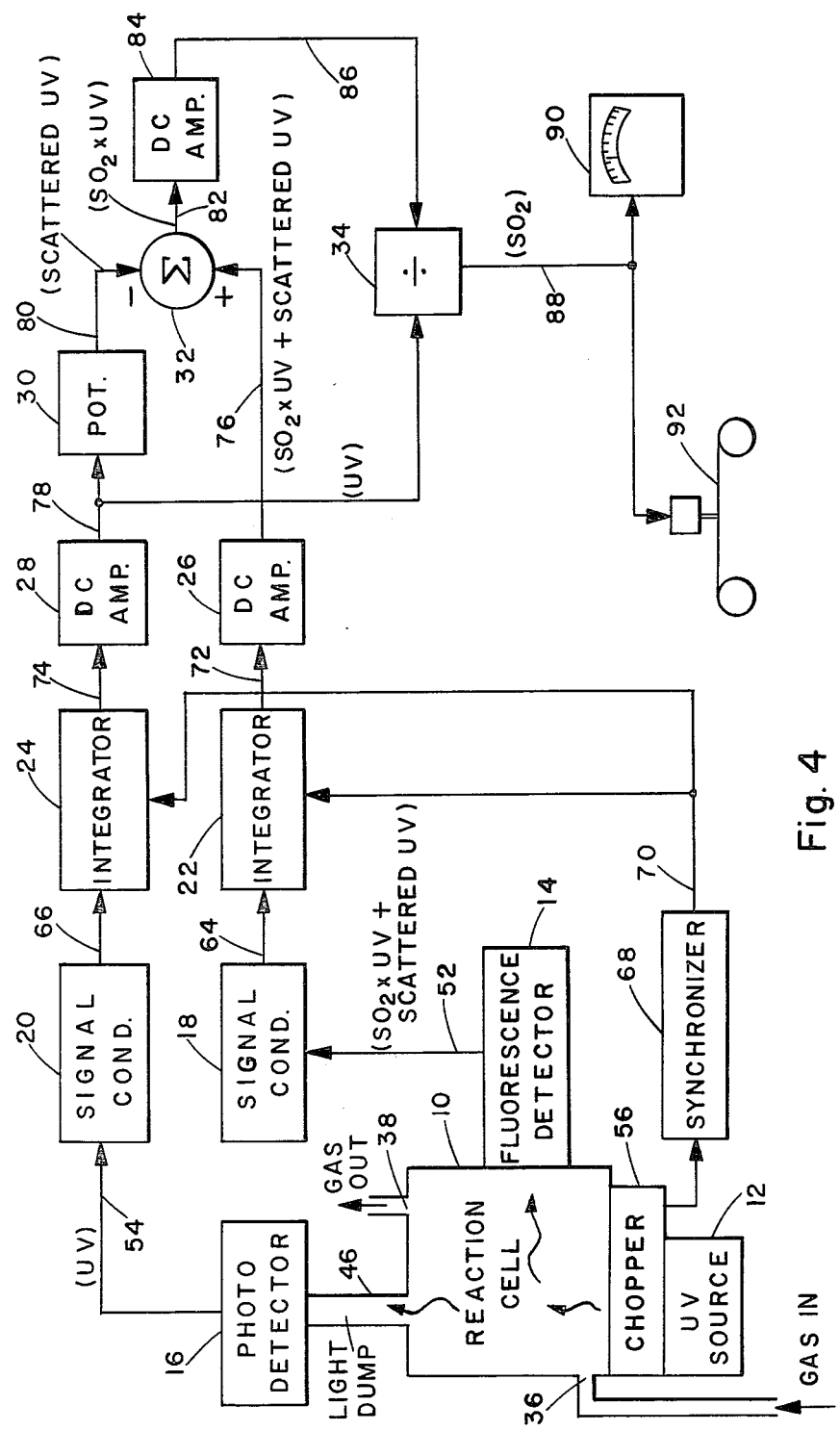
FIG. 4 is a schematic block diagram of a preferred embodiment of the fluorescent gas analyzer.

The potentiometer 30 is coupled to the DC amplifier 28 for factoring the fourth signal on line 78 to provide a fifth signal on line 80 having a level bearing the given proportional relationship to the quantity of the scattered UV light detected by the photomultiplier tube 14 over the predetermined interval. The manner in which the potentiometer 30 is adjusted to so factor the fourth signal on line 78 is discussed below following the description of the reminder of the circuit shown in FIG. 4.

A summing circuit 32 is coupled to the DC amplifier 26 and the potentiometer 30 for providing a sixth signal on line 82 having a level bearing the given proportional relationship to the difference between the levels of the third signal on line 76 and the fifth signal on line 80, to thereby provide a signal on line 82 having a level bearing the given proportional relationship to the quantity of fluorescence detected by the photomultiplier tube 14 over the predetermined interval. In this manner the scattered UV light is prevented from affecting the ultimate output signal from the fluorescent gas analyzer.

The sixth signal on line 82 is passed through a DC amplifier 84 which contains a fine calibration adjustment. An amplified sixth signal is provided by the DC amplifier 84 on line 86.

The divider circuit 34 divides the sixth signal on line 86 by the fourth signal on line 78 to provide a seventh signal on line 88 having a level that is proportional to the concentration of $SO_2$ that fluoresces within the reaction cell 10 in response to the UV light from the UV lamp 12 over the predetermined interval. In this manner the output signal of the fluorescent gas analyzer on line 88 is made independent of variations in the intensity of the UV light radiated by the UV lamp 12.

In order to factor the fourth signal on line 78 to provide a fifth signal on line 80 that has a level bearing the given proportional relationship to the quantity of scattered UV light detected by the photomultiplier 14 over the predetermined interval, the potentiometer 30 is adjusted to reduce the level of the fourth signal on line 78 to cause the fifth signal on line 80 to have a level that causes the level of the seventh signal on line 88 to be zero when a gas containing no fluorescent compounds is radiated by UV light within the reaction cell 10.

The output signal on line 88 is fed to an indicating device, such as a meter 90 or a strip chart recorder 92, to provide an indication of the concentration of $SO_2$ in the carrier gas.

We claim:

1. A fluorescent gas analyzer, comprising;
   a reaction cell having inlet and outlet ports for enabling gas flow through the cell;
   an excitation energy source coupled to the reaction cell for radiating the interior of the cell with excitation energy that causes a given gas to fluoresce in a given wavelength;
   a first detector coupled to the reaction cell for detecting fluorescence in the given wavelength and for providing a first signal that is proportional to the intensity of said detected fluorescence and the intensity of detected scattered excitation energy radiated from the excitation energy source;
   a second detector coupled to the reaction cell for detecting excitation energy radiated from the excitation energy source, and for providing a second signal that is proportional to said detected excitation energy;
   a first circuit coupled to the first detector for responding to the first signal to provide a third signal having a level bearing a given proportional relationship to the sum of the quantity of said fluorescence detected by the first detector over a predetermined interval and the quantity of said scattered excitation energy detected by the first detector over said predetermined interval;
   a second circuit coupled to the second detector for responding to the second signal to provide a fourth signal having a level bearing said given proportional relationship to the quantity of said excitation energy detected by the second detector over said predetermined interval;
   a third circuit coupled to the second circuit for factoring the fourth signal to provide a fifth signal having a level bearing said given proportional relationship to the quantity of said scattered excitation energy detected by the first detector over said predetermined interval;
   a fourth circuit coupled to the first and third circuits for providing a sixth signal having a level bearing said given proportional relationship to the difference between the levels of the third and fifth signals, to thereby provide a signal having a level bearing said given proportional relationship to the quantity of said fluorescence detected by the first detector over said predetermined interval; and
   a fifth circuit for dividing the sixth signal by the fourth signal to provide a seventh signal having a level that is proportional to the concentration of said gas that fluoresces within the reaction cell in response to said excitation energy over said predetermined interval.

2. A fluorescent gas analyzer according to claim 1, wherein the third circuit comprises a potentiometer for reducing the level of the fourth signal to provide a said fifth signal that has a level that causes the level of the seventh signal to be zero when a gas containing no fluorescent compounds is radiated by excitation energy within the reaction cell.

3. A fluorescent gas analyzer according to claim 1, wherein the first and second circuits respectively comprises integrators for continuously integrating the first and second signals over said predetermined interval.

4. A fluorescent gas analyzer according to claim 3, further comprising;
   a chopper coupled to the excitation energy source for causing said excitation energy that is radiated into the reaction cell to be pulsed at a predetermined rate for enhancing the signal-to-noise ratio of the first and second signals; and
   a synchronizer coupled to the chopper and the integrators for providing a synchronization signal having said predetermined rate to the integrators for synchronizing said integration with said pulses of excitation energy.

5. A fluorescent gas analyzer according to claim 1, wherein the excitation energy source comprises a source of ultraviolet radiation.

6. A fluorescent gas analyzer according to claim 1 or 5 wherein the first detector is coupled to the reaction cell for detecting fluorescence from sulfur dioxide.

7. A fluorescent gas analyzer according to claims 1 or 5, further comprising;
   a chopper coupled to the excitation energy source for causing said excitation energy that is radiated into the reaction cell to be pulsed at a predetermined rate for enhancing the signal-to-noise ratio of the first and second signals.

8. A fluorescent gas analyzer according to claim 1, wherein the second detector and the excitation energy source are coaxially positioned on opposite sides of the reaction cell, and the first detector is positioned to detect primarily fluorescence along an axis that is orthogonal to the common axis of the second detector and the excitation energy source.

* * * * *

REEXAMINATION CERTIFICATE (1085th)
United States Patent [19]
Wright et al.

[11] B1 4,260,890
[45] Certificate Issued    Jun. 27, 1989

[54] FLUORESCENT GAS ANALYZER

[75] Inventors: Steven A. Wright, San Diego; Donald A. Watts, Ramona, both of Calif.

[73] Assignee: Monitor Labs, Incorporated, San Diego, Calif.

Reexamination Request:
No. 90/001,384, Nov. 30, 1987

Reexamination Certificate for:
Patent No.: 4,260,890
Issued: Apr. 7, 1981
Appl. No.: 51,498
Filed: Jun. 25, 1979

[51] Int. Cl.⁴ .......................... G01J 1/42; G01N 21/64
[52] U.S. Cl. ........................................ 250/373; 250/435
[56] References Cited

U.S. PATENT DOCUMENTS 3,826,692  7/1974  Woodroffe et al. ............... 250/373
3,906,622  9/1975  Okabe et al. ...................... 250/304
4,079,256  3/1978  Ford et al. ........................ 250/343

OTHER PUBLICATIONS

West, "Developments in Photophysical Instrumentation A Spectrofluorimeter For Routine Analysis,-"*American Laboratory*, Nov. 1975, pp. 57-67.
Perkin-Elmer, *Instructions Model MPF-2A Spectrophotofluorimeter*, Oct. 1967.

*Primary Examiner*—Constantine Hannaher

[57] ABSTRACT

A fluorescent gas analyzer that provides a DC output signal that is proportional to the concentration of a given gas that fluoresces within a reaction cell over a predetermined interval is disclosed. The analyzer includes a detector combination and a compensation circuit that prevent the output signal from being affected by scattered excitation energy detected by the fluorescence detector or by variations in the excitation energy. The analyzer is particularly adapted for detecting fluorescence from $SO_2$ that is excited by UV radiation.

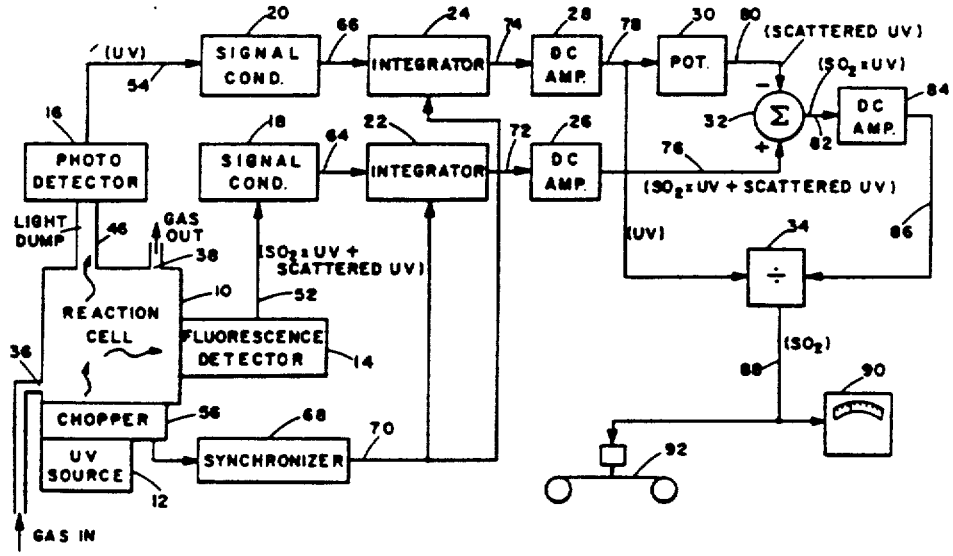

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-8 are cancelled.

* * * * *